United States Patent
Yalla et al.

(10) Patent No.: US 12,279,979 B2
(45) Date of Patent: Apr. 22, 2025

(54) DURABILITY TEST SYSTEM FOR REPETITIVE LOADING OF A PROSTHETIC SOCKET

(71) Applicant: Rosalind Franklin University of Medicine & Science, North Chicago, IL (US)

(72) Inventors: Sai V. Yalla, North Chicago, IL (US); Sunjung Kim, North Chicago, IL (US); Noah J. Rosenblatt, North Chicago, IL (US)

(73) Assignee: ROSALIND FRANKLIN UNIVERSITY OF MEDICINE AND SCIENCE, North Chicago, IL (US)

( * ) Notice: Subject to any disclaimer, the term of this patent is extended or adjusted under 35 U.S.C. 154(b) by 274 days.

(21) Appl. No.: 17/936,539

(22) Filed: Sep. 29, 2022

(65) Prior Publication Data

US 2023/0095380 A1    Mar. 30, 2023

Related U.S. Application Data

(60) Provisional application No. 63/250,148, filed on Sep. 29, 2021.

(51) Int. Cl.
*A61F 2/76* (2006.01)
*G01N 3/06* (2006.01)
(Continued)

(52) U.S. Cl.
CPC .............. *A61F 2/76* (2013.01); *G01N 3/06* (2013.01); *G01N 3/08* (2013.01); *G01N 3/32* (2013.01);
(Continued)

(58) Field of Classification Search
CPC ............... A61F 2/76; A61F 2002/7635; A61F 2002/7695; A61F 2/7695; G01N 3/06;
(Continued)

(56) References Cited

U.S. PATENT DOCUMENTS

| 2,366,238 A | 1/1945 | Witt |
| 4,075,898 A | 2/1978 | Carlson, Jr. |
| 9,186,224 B2 | 11/2015 | McCloskey |

FOREIGN PATENT DOCUMENTS

IT    202100006293 A1 *    9/2022

OTHER PUBLICATIONS

Heeluxe, "The Time Machine Shoe Durability Test is Here!", https://www.heeluxe.com/the-time-machine-shoe-durability-test-is-here/, retrieved from the Internet on Sep. 29, 2022.

\* cited by examiner

*Primary Examiner* — Robert R Raevis
(74) *Attorney, Agent, or Firm* — McDonnell Boehnen Hulbert & Berghoff LLP

(57) ABSTRACT

The present disclosure relates to a system for repetitive loading of a prosthetic socket to test the durability of the prosthetic socket. The system includes a base and a load cell coupled to the base. The system further includes a first coupling mechanism positioned vertically above the load cell, and a second coupling mechanism positioned vertically above the first coupling mechanism. The first coupling mechanism is configured to be removably coupled to a first end of the prosthetic socket, and the second coupling mechanism is configured to be removably coupled to a second end of the prosthetic socket. The system further includes a rod having a first end and a second end opposite the first end. The first end of the rod is coupled to the second coupling mechanism. The system further includes a motor coupled to the second end of the rod, a support structure extending (Continued)

vertically from the base, and an actuator coupled to the support structure such that the actuator is positioned vertically above the second coupling mechanism. The system further includes a curved rail coupled to the actuator and positioned between the actuator and the second coupling mechanism. The curved rail is configured to contact the second coupling mechanism along an arc defined by the curved rail such that the second coupling mechanism moves along the arc when the motor moves the rod.

20 Claims, 2 Drawing Sheets

(51) Int. Cl.
*G01N 3/08* (2006.01)
*G01N 3/32* (2006.01)

(52) U.S. Cl.
CPC ............... *A61F 2002/7635* (2013.01); *A61F 2002/7695* (2013.01); *G01N 2203/0005* (2013.01); *G01N 2203/0019* (2013.01); *G01N 2203/06* (2013.01)

(58) Field of Classification Search
CPC .... G01N 3/08; G01N 3/32; G01N 2203/0005; G01N 2203/0019; G01N 2203/06; G01N 3/20
USPC .................. 73/788–790, 794, 795, 806, 808, 73/812–818, 849, 853, 854, 865.3, 865.4, 73/865.9, 866; 623/66.1
See application file for complete search history.

DURABILITY TEST SYSTEM FOR REPETITIVE LOADING OF A PROSTHETIC SOCKET

RELATED APPLICATIONS

This application claims priority to U.S. Provisional Application No. 63/250,148 entitled "Durability Test System for Repetitive Loading of a Prosthetic Socket," filed on Sep. 29, 2021, the contents of which are hereby incorporated by reference in its entirety.

GOVERNMENT RIGHTS

This invention was made with government support under Grant No. W81XWH2010175, awarded by the U.S. Department of Defense (DoD). The government has certain rights in the invention.

TECHNICAL FIELD

The present disclosure relates to a durability test system for repetitive loading of a prosthetic socket.

BACKGROUND

Unless otherwise indicated herein, the materials described in this section are not admitted to be prior art to the claims in this application.

Major extremity amputation is a prevalent conflict injury—over 1,700 service-related amputations were performed during Operation Iraqi Freedom, Operation New Dawn and Operation Enduring Freedom—and over 50,000 new amputations are performed in the VHA annually. For a new amputee, early provision and acceptance of a prosthesis is critical to successful rehabilitation. The use of Immediate Post-Operative Prosthesis (IPOP) and preparatory prosthesis can significantly help reduce phantom limb pain and sensation, increase the acceptance rate of and satisfaction with a prosthesis, reduce complications and in turn promote overall improved quality of life and prosthetic function. However, for a variety of reasons, prosthetic fittings do not always start early on following amputation. For example, prosthetic labs are not generally part of in-patient hospital settings, limiting access to these services in the acute post-amputation stage. Even if prosthetic services are outsourced, traditional methods of prosthetic fitting can take time.

3D printing of prosthetic sockets (and eventually, IPOPs) offer the potential for rapid fabrication within the acute-care setting. Simple scanners and software applications can be used to scan the limb that can be emailed to a skilled prosthetists and then designed, printed and returned to the patient within 24 hours. Moreover, the socket can be quickly and cheaply re-fabricated as the limb continues to shrink. In the long-term, introducing 3D printed sockets into early rehabilitation may help to optimize early rehabilitation outcomes. This would have a direct benefit to military members, veterans, and their families is that patients will be more accepting of prosthesis and have improved outcomes. In addition, the use of 3D printing opens up the possibility of customizing sockets to the individual, e.g., providing a passive limb-socket interface with variable flexibility and stiffness achieved through depositing different materials and/or material thicknesses based on limb anatomy, to maximize prosthetic comfort and fit. Given that 57% of traumatic amputee's report comfort and fit as a key barrier to prosthetic use this long-term goal has potential to promote prosthetic use and outcomes associated with increased physical activity. Despite the promise that 3D printing holds in terms of reducing the time to initial fitting and in turn improving early rehabilitation outcomes, the extent to which 3D printed devices are safe for daily use remains unknown.

The concept of durability is critical to understand for these new emerging materials and methods. Unlike standard lamination processes, 3D printing involves fusing together layers of materials, which may affect durability. Nonetheless, it is entirely possible that 3D printed sockets are at least durable enough for use in short-term early rehabilitation. Quantifying the durability of 3D printed sockets will help to establish standards that are necessary before it is possible to conduct a trial evaluating outcomes with these devices.

Durability testing involves exposing sockets to continuous, controlled, cyclic forces (loads) within a laboratory setting and observing how the shape of the socket changes over time (with increasing number of loading cycles). What is needed is the ability to study durability via fatigue testing while simulating walking. Currently, nothing exists for such testing of sockets.

SUMMARY

In view of the foregoing, the present disclosure provides an independent durability test system for repetitive loading of a prosthetic socket with radial and axial range of motion expandable and contractible at either end. The system is used in combination with a slotted link mechanism and a parallelogram mechanism, which can be controlled relative to each other to successfully simulate walking, jumping or running patterns.

Thus, in a first aspect, the present disclosure provides a system for repetitive loading of a prosthetic socket. The system includes (i) a base, (ii) a load cell coupled to the base, (iii) a first coupling mechanism positioned vertically above the load cell, wherein the first coupling mechanism is configured to be removably coupled to a first end of the prosthetic socket, (iv) a second coupling mechanism positioned vertically above the first coupling mechanism, wherein the second coupling mechanism is configured to be removably coupled to a second end of the prosthetic socket, (v) a rod having a first end and a second end opposite the first end, wherein the first end of the rod is coupled to the second coupling mechanism, (vi) a motor coupled to the second end of the rod, (vii) a support structure extending vertically from the base, (viii) an actuator coupled to the support structure such that the actuator is positioned vertically above the second coupling mechanism, and (ix) a curved rail coupled to the actuator and positioned between the actuator and the second coupling mechanism, wherein the curved rail is configured to contact the second coupling mechanism along an arc defined by the curved rail such that the second coupling mechanism moves along the arc when the motor moves the rod.

In a second aspect, the present invention provides a method for testing a durability of a prosthetic socket, the method comprising: (i) positioning a prosthetic socket into the system of the first aspect, (ii) applying a compressive force to the prosthetic socket, and (iii) activating the motor to generate a cyclic motion that pushes and pulls the rod to thereby push and pull the second coupling mechanism along the arc of the curved rail for a number of cycles.

These as well as other aspects, advantages, and alternatives, will become apparent to those of ordinary skill in the

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The exemplary embodiments described herein are not meant to be limiting. It will be readily understood that the aspects of the present disclosure, as generally described herein and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Figure 2:
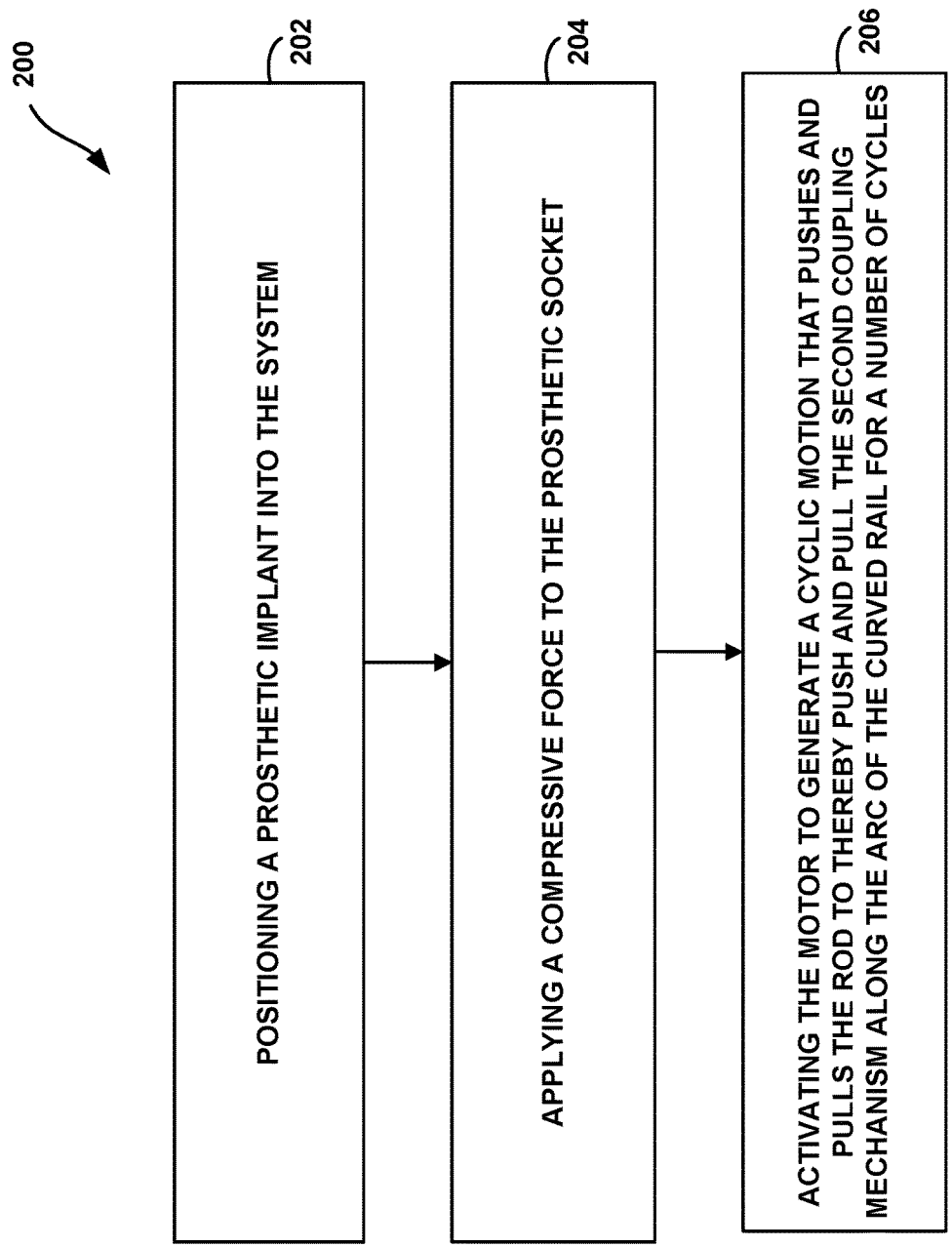
FIG. 2 is a flowchart illustrating an example method for measuring a stability of an implant system, according to an example embodiment.

In FIG. 2, referred to above, the blocks may represent operations and/or portions thereof and lines connecting the various blocks do not imply any particular order or dependency of the operations or portions thereof. It will be understood that not all dependencies among the various disclosed operations are necessarily represented. FIG. 2 and the accompanying disclosure describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, those skilled in the art will appreciate that not all operations described need be performed.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

As used herein, with respect to measurements and angles, "about" means +/−5%.

The present disclosure provides a device to test prosthetic sockets made from different materials. For cyclic durability testing at half the failure load, the goal is to simulate the loading pattern of walking onto the socket. Such cyclic durability testing may be performed at half the failure load in one example, although any load may be used. In order to achieve that loading pattern of walking, in one particular example a prosthetic socket should be set at a positive angle of about +23 degrees from vertical to simulate heel strike and about −5 degrees from vertical to simulate toe off. The particular angles may be adjusted based on the particular pylon being used. The present disclosure provides a stand-alone cyclic testing rig so that the socket will traverse this range of angles during each loading cycle at a fixed load or variable loading by adjusting a compressive force transmitted by the testing system to the prosthetic socket. This compressive force may be controlled by a software program (e.g., Labview) that is configured to adjust the loads based on the feedback received by a load cell at the bottom of the testing system.

Figure 1:
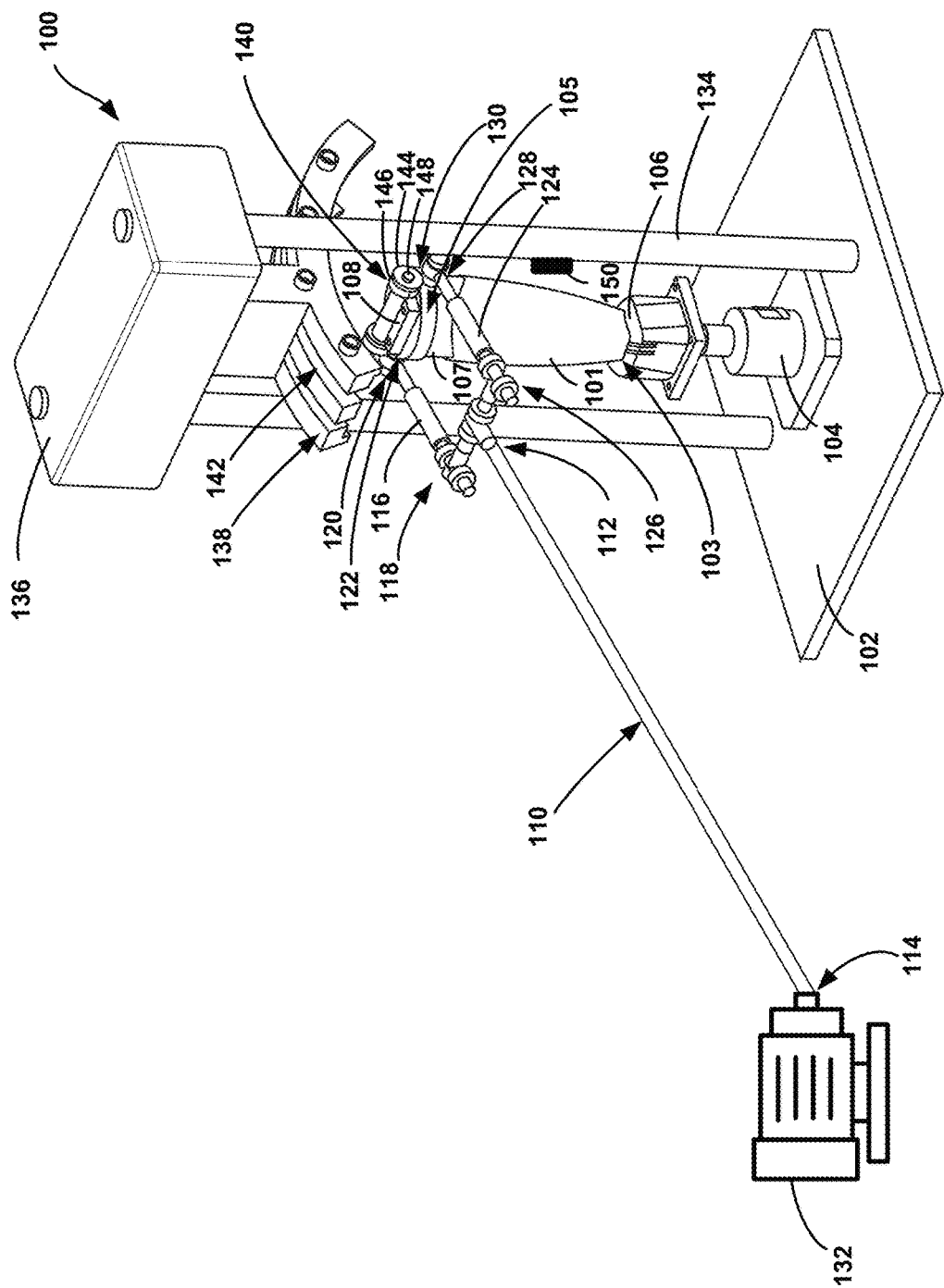
FIG. 1 illustrates a perspective view of a system for repetitive loading of a prosthetic socket, according to an exemplary embodiment.

With reference to the Figures, FIG. 1 illustrates a system 100 for repetitive loading of a prosthetic socket 101. As shown in FIG. 1, the system 100 includes a base 102 and a load cell 104 coupled to the base 102. The system 100 further includes a first coupling mechanism 106 positioned vertically above the load cell 104. The first coupling mechanism 106 is configured to be removably coupled to a first end 103 of the prosthetic socket 101. In one example, the first coupling mechanism 106 comprises a clevis rod. In another example, the first coupling mechanism 106 comprises one or more screws. Other coupling mechanisms as possible as well.

The system 100 further includes a second coupling mechanism 108 positioned vertically above the first coupling mechanism 106. The second coupling mechanism 108 is configured to be removably coupled to a second end 105 of the prosthetic socket 101. In one example, the second coupling mechanism 108 includes one or more screws. Other coupling mechanisms as possible as well. In one example, a limb liner 107 is placed on the second end 105 of prosthetic socket 101, and then the prosthetic socket 101 is pressed onto the limb liner 107. In one example, such a limb liner 107 is locked to the prosthetic socket 101 via a pin lock mechanism.

The system 100 further includes a rod 110 having a first end 112 and a second end 114 opposite the first end 112. The first end 112 of the rod 110 is coupled to the second coupling mechanism 108. In one example, a length of the rod 110 is adjustable. In one such example, the rod 110 comprises an inner rod and an outer rod that are able to telescope with respect to one another. Other arrangements are possible as well. Such an arrangement enables forces applied to the prosthetic socket 101 to be adjusted for particular use cases, as discussed in additional detail below.

In one example, the first end 112 of the rod 110 is directly coupled to the second coupling mechanism 108. In another example, the first end 112 of the rod 110 is indirectly coupled to the second coupling mechanism 108. In one such example, as shown in FIG. 1, the system 100 further includes a second rod 116 having a first end 118 coupled to the first end 112 of the rod 110 and a second end 120 coupled to a first side 122 of the second coupling mechanism 108. In such an example, the system 100 further includes a third rod 124 having a first end 126 coupled to the first end 112 of the rod 110 and a second end 128 coupled to a second side 130 of the second coupling mechanism 108. Such an example may transfer force more uniformly from the rod 110 to the prosthetic socket 101.

The system 100 further includes a motor 132 coupled to the second end 114 of the rod 110. In one example, the motor 132 is positioned on the base 102. In another example, the motor 132 is positioned on a structure (such as a table) adjacent the base 102. The motor 132 may comprise an electric motor and may include a gearbox to achieve the necessary stress and torque requirements for the system 100 to operate properly. The system 100 further includes a support structure 134 extending vertically from the base 102. As shown in FIG. 1, the support structure 134 may comprise a pair of rods configured to be positioned on either side of the prosthetic socket 101, although other support structures are possible as well. The system 100 further includes an actuator 136 coupled to the support structure 134 such that the actuator 136 is positioned vertically above the second coupling mechanism 108. The system 100 further includes a curved rail 138 coupled to the actuator 136 and positioned between the actuator 136 and the second coupling mechanism 108. The actuator 136 is configured to adjust a distance between the curved rail 138 and the second coupling mechanism 108. In use, the curved rail 138 is configured to contact the second coupling mechanism 108 along an arc defined by the curved rail 138 such that the second coupling mechanism 108 moves along the arc when the motor 132 moves the rod 110.

In use, the motor 132 generates a cyclic motion that pushes and pulls the rod 110 to thereby push and pull the second coupling mechanism 108 along the arc defined by the bottom surface of the curved rail 138. In one example, the first end 103 of the prosthetic socket 101 is fixed with respect to the base, while the second end 105 of the prosthetic socket 101 moves along the arc defined by the bottom surface of the curved rail 138 during the testing cycle. In one example, the motor 132 is configured to cause a range of motion of the prosthetic socket 101 from about −25 degrees with respect to a longitudinal axis of the prosthetic socket 101 (simulating a toe-off) to about 25 degrees with respect to the longitudinal axis of the prosthetic socket 101 (simulating a heel strike). In another example, the motor is configured to cause a range of motion of the prosthetic socket 101 from about −5 degrees with respect to a longitudinal axis of the prosthetic socket 101 (simulating a toe-off) to about 23 degrees with respect to the longitudinal axis of the prosthetic socket 101 (simulating a heel strike). In one example, the particular angles may be adjusted based on the particular prosthetic socket 101 being used. For example, as discussed above, the length of the rod 110 may be adjustable to thereby adjust the forces from the motor 132 applied to the prosthetic socket 101.

In one example, as shown in FIG. 1, the system 100 further includes at least one rotatable component 140 coupled to the second coupling mechanism 108. In such an example, the at least one rotatable component 140 is configured to contact the curved rail 138. In one such example, the curved rail 138 includes at least one groove 142 configured to receive the at least one rotatable component 140. In one particular example, as shown in FIG. 1, the at least one rotatable component 140 comprises a cylindrical disk 144 with a plurality of ball bearings 146. The cylindrical disk 144 may be secured to the second coupling mechanism 108 via a pin 148 such that the cylindrical disk 144 can rotate with respect to the second coupling mechanism 108. In one example, as shown in FIG. 1, the at least one rotatable component 140 extends vertically from the second coupling mechanism 108 such that only the at least one rotatable component 140 contacts and moves along the arc defined by the bottom surface of the curved rail 138 when the motor 132 is activated.

In one example, as shown in FIG. 1, the at least one rotatable component 140 comprises a first rotatable component positioned on the first side 122 of the second coupling mechanism 108 and a second rotatable component positioned on the second side 130 of the second coupling mechanism 108. Having two rotatable components may help to ensure the movement of the prosthetic socket 101 in an x-y plane.

In use, the actuator 136 is configured to provide a compressive force between the curved rail 138 and the second coupling mechanism 108. In one example, the compressive force comprises about one half of a static failure load of the prosthetic socket 101. In such an example, the compressive force may be constant throughout a number of cycles. In another example, the compressive force is varied throughout the number of cycles. In one such example, the compressive force applied by the actuator 136 may be adjusted based on a measurement from the load cell 104.

In one example, the system 100 includes a laser displacement sensor 150 for measuring a deformation of the prosthetic socket 101. The laser displacement sensor 150 may be capable of accurately measuring displacement up to about 6 μm. In one example, the laser displacement sensor 150 is configured to measure depth. In such an example, special indentations can either be engraved or glued on top of the prosthetic socket 101. A software program may be configured to read the number of indentations passed using the laser displacement sensor 150 and the combination of the software program measuring indentations using laser displacement sensor 150 measures the distance travelled by the prosthetic socket 101. In another example, the displacement of the prosthetic socket 101 can be measured by the actuator 136 so that no separate displacement sensor 150 is required.

FIG. 2 is a block diagram of an example method for testing a durability of a prosthetic socket. Method 200 shown in FIG. 2 presents an embodiment of a method that could be used by the system 100 as described above. Method 200 may include one or more operations, functions, or actions as illustrated by one or more of blocks 202-206.

Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 200 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Initially, at block 202, the method 200 includes positioning a prosthetic socket 101 into the system 100 described above in relation to FIG. 1. At block 202, the method 200 includes applying a compressive force to the prosthetic socket 101. At block 206, the method 200 includes activating the motor 132 to generate a cyclic motion that pushes and pulls the rod 110 to thereby push and pull the second coupling mechanism 108 along the arc of the curved rail for a number of cycles.

In one example, as discussed above, the compressive force is applied to the prosthetic socket 101 via the actuator 136. In one example, the compressive force comprises about one half of a static failure load of the prosthetic socket 101. In such an example, the compressive force may be constant throughout the number of cycles. In another example, the compressive force is varied throughout the number of cycles.

In one example, the method 200 further comprises evaluating a durability of the prosthetic socket 101 after the number of cycles. The durability of the prosthetic socket 101 may be determined via a laser displacement sensor 150, as discussed above. In another example, the durability of the prosthetic socket 101 may be determined by a finite element analysis. In another example, the durability of the prosthetic socket 101 may be determined by a visual analysis. Other durability evaluations are possible as well.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Because many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A system for repetitive loading of a prosthetic socket, the system comprising:
a base;
a load cell coupled to the base;
a first coupling mechanism positioned vertically above the load cell, wherein the first coupling mechanism is configured to be removably coupled to a first end of the prosthetic socket;
a second coupling mechanism positioned vertically above the first coupling mechanism, wherein the second coupling mechanism is configured to be removably coupled to a second end of the prosthetic socket;
a rod having a first end and a second end opposite the first end, wherein the first end of the rod is coupled to the second coupling mechanism;
a motor coupled to the second end of the rod;
a support structure extending vertically from the base;
an actuator coupled to the support structure such that the actuator is positioned vertically above the second coupling mechanism; and
a curved rail coupled to the actuator and positioned between the actuator and the second coupling mechanism, wherein the curved rail is configured to contact the second coupling mechanism along an arc defined by the curved rail such that the second coupling mechanism moves along the arc when the motor moves the rod.

2. The system of claim 1, wherein the motor generates a cyclic motion that pushes and pulls the rod to thereby push and pull the second coupling mechanism along the arc of the curved rail.

3. The system of claim 1, wherein the first end of the rod is indirectly coupled to the second coupling mechanism.

4. The system of claim 3, the system further comprising:
a second rod having a first end coupled to the first end of the rod and a second end coupled to a first side of the second coupling mechanism; and
a third rod having a first end coupled to the first end of the rod and a second end coupled to a second side of the second coupling mechanism.

5. The system of claim 1, further comprising:
at least one rotatable component coupled to the second coupling mechanism, wherein the at least one rotatable component is configured to contact the curved rail.

6. The system of claim 5, wherein the curved rail includes at least one groove in a bottom surface of the curved rail configured to receive the at least one rotatable component.

7. The system of claim 6, wherein the at least one groove in the bottom surface of the curved rail comprises two grooves, and wherein the at least one rotatable component is configured to be received between the two grooves.

8. The system of claim 5, wherein the at least one rotatable component comprises a cylindrical disk with a plurality of ball bearings.

9. The system of claim 5, wherein the at least one rotatable component extends vertically from the second coupling mechanism such that only the at least one rotatable component contacts and moves along the arc when the motor moves the rod.

10. The system of claim 5, wherein the at least one rotatable component comprises a first rotatable component positioned on a first side of the second coupling mechanism and a second rotatable component positioned on a second side of the second coupling mechanism.

11. The system of claim 1, wherein the actuator is configured to adjust a compressive force between the curved rail and the second coupling mechanism.

12. The system of claim 1, wherein the motor is configured to cause a range of motion of the prosthetic socket from about −25 degrees with respect to a longitudinal axis of the prosthetic socket to about 25 degrees with respect to the longitudinal axis of the prosthetic socket.

13. The system of claim 1, wherein the motor is configured to cause a range of motion of the prosthetic socket from about −5 degrees with respect to a longitudinal axis of the prosthetic socket to about 23 degrees with respect to the longitudinal axis of the prosthetic socket.

14. The system of claim 1, wherein about one half of a static failure load is applied to the prosthetic socket by the actuator during operation of the motor.

15. The system of claim 1, wherein a length of the rod is adjustable.

16. A method for testing a durability of a prosthetic socket, the method comprising:
positioning a prosthetic socket into the system of claim 1;
applying a compressive force to the prosthetic socket; and
activating the motor to generate a cyclic motion that pushes and pulls the rod to thereby push and pull the second coupling mechanism along the arc of the curved rail for a number of cycles.

17. The method of claim 16, wherein the compressive force is applied to the prosthetic socket via the actuator.

18. The method of claim 16, wherein the compressive force comprises about one half of a static failure load of the prosthetic socket.

19. The method of claim 16, further comprising:
evaluating a durability of the prosthetic socket after the number of cycles.

20. The method of claim 16, wherein the compressive force is varied throughout the number of cycles.

* * * * *